United States Patent [19]

Raisz et al.

[11] Patent Number: 5,391,567
[45] Date of Patent: Feb. 21, 1995

[54] METHOD FOR TREATING HYPERCALCEMIA USING SALTS OF TNCA

[75] Inventors: Lawrence G. Raisz, Farmington, Conn.; Carlos M. Samour, Newport, R.I.

[73] Assignee: Macrochem Corporation, Lexington, Mass.

[21] Appl. No.: 122,173

[22] Filed: Sep. 17, 1993

Related U.S. Application Data

[63] Continuation of Ser. No. 987,994, Dec. 9, 1992, abandoned, which is a continuation of Ser. No. 808,094, Dec. 16, 1991, abandoned, which is a continuation-in-part of Ser. No. 739,779, Jul. 31, 1991, abandoned, which is a continuation of Ser. No. 86,848, Aug. 19, 1987, abandoned, which is a continuation-in-part of Ser. No. 903,385, Sep. 3, 1986, abandoned.

[51] Int. Cl.$^6$ .............................................. A61K 31/38
[52] U.S. Cl. .................................................... 514/443
[58] Field of Search ........................................ 514/443

[56] References Cited

U.S. PATENT DOCUMENTS

| | | | |
|---|---|---|---|
| 4,101,668 | 7/1978 | Samour et al. | 514/443 |
| 4,125,621 | 11/1978 | Samour et al. | 514/443 |
| 4,185,108 | 1/1980 | Samour et al. | 514/419 |
| 4,434,163 | 2/1984 | Lombardino | 514/222 |

OTHER PUBLICATIONS

Raisz et al, Calcif Tissue Int. (1985) 37:556–559, "Effects of Thionapthene 2–Carboxylic Acid and Related Compounds on Bone Resorption in Organ Culture".

Johannesson et al, Endocrinology, vol. 117, No. 4 (1985), pp. 1508–1511, "Thionapthene-2-Carboxylic Acid: A New Antihypercalcemic Agent".

*Primary Examiner*—Mary C. Lee
*Assistant Examiner*—Jacqueline Haley
*Attorney, Agent, or Firm*—Sherman and Shalloway

[57] ABSTRACT

Malignancy-induced hypercalcemia is treated with thionapthene-2-carboxylic acid (TNCA) and the pharmaceutically acceptable salts thereof. The treatment is also effective in tumor bearing hosts even before there is significant abnormal serum calcium levels. There is no "escape" from the hypocalcemic effects of these compounds as with e.g., calcitonin. The useful dosage in humans for TNCA itself ranges from about 1 to about 60 mg/kg/day preferably from about 2 to about 30 mg/kg/day and more preferably from about 5 to about 20 mg/kg/day (20 mg is approximately 0.106 mmol) Orally administered TNCA or salts thereof, is a much desired and obviously clinically advantageous mode of administering compounds to control or ameliorate hypercalcemia.

7 Claims, No Drawings

METHOD FOR TREATING HYPERCALCEMIA USING SALTS OF TNCA

This application is a continuation of application Ser. No. 7/987,994, filed Dec. 9, 1992, now abandoned which is a continuation of application Ser. No. 07/808,094, filed Dec. 16, 1991, now abandoned, which is a continuation-in-part of application Ser. No. 07/739,779, filed Jul. 31, 1991 abandoned, which is a continuation of application Ser. No. 07/086,848, filed Aug. 19, 1987, now abandoned, which is a continuation in part of application Ser. No. 06/903,385, filed Sep. 3, 1986, now abandoned.

The invention relates to a method and compositions for treating hypercalcemia in an animal host utilizing thionaphthene-2-carboxylic acid (TNCA) and the pharmaceutically acceptable salts thereof.

BACKGROUND OF THE INVENTION

The depletion of bone or skeletal calcium is a characteristic of osteoporosis where the bone is histologically normal. The loss may be of the cortical and/or trabecular bone mass, the former constituting about 80% of skeletal bone and forms the dense outer layer of bone; while trabecular bone constitutes the interior of bone and forms a reticulated matrix which provides such bone with a greater surface area per unit volume than cortical bone, and consequently, a much higher rate of bone resorption and formation (turnover); loss about 8×faster than is cortical bone. Before bone loss begins, there is a dynamic balance or coupling between formation and resorption of bone with new bone being continuously formed and old bone resorbed. After some 30 or 40 years uncoupling begins. During coupling there is a balance between the action of the osteoclasts and the osteoblasts. A negative balance results in osteoporosis. It is not clearly established whether this uncoupling is due to a deficiency of osteoblasts (formation) or to an increase in osteoclast (resorption) activity; especially since it is not universally found that osteoblast dysfunction results in osteoporosis. Clinically, the manifestation of the disease are low-energy fractures. Of the therapies used to reduce the risk of fractures by reducing the loss of bone are (1) increasing dietary calcium, (2) use of fluorides, (3) combination of calcium and fluorides, (4) estrogen, (5) thiazides, (6) calcitonin, (7) mithramycin, (8) certain phosphonates, and (9) a variety of inhibitors for thyroid hormone (RTH)-stimulated bone resorption such as thiophene 2-carboxylic, indole-2-carboxylic, thionaphthene-2-carboxylic acid among others. While there is no clinical hypercalcemic condition present in osteoporosis among the new approaches to the treatment of osteoporosis has been the use of materials with hypoccalcemic activity, i.e., lowering of the serum calcium, which is believed to be related to an indicative of a decrease in the rate of bone resorption. Calcitonin, mithramycin (an antibiotic) and certain phosphonates are representative hypocalcemic agents, but adverse effects and lack of effectiveness in bone-loss prevention associated with the use of such agents, make continued research necessary.

In recent U.S. Pat. Nos. 4,101,668 (issued Jul. 18, 1978), 4,125,621 (issued Nov. 14, 1978) and 4,185,108 (issued Jan. 22, 1980), all three having as inventors C. M. Samour and J. A. Vida, there are disclosed a wide variety of benzo-heterocyclic compounds for use as antiosteoporotic agents. Among the specific compounds described are thionaphthene-2-carboxylic acid, thionaphthene-3-carboxylic acid, thionaphthene-4-carboxylic acid, dibenzothiophene-4-carboxylic acid, thioxanthene-9-one-4-carboxylic acid and indole-2-carboxylic acid.

The compounds are compared to thyrocalcitonin (TCT), the latter, a bone-remodeling hormone which is capable of reducing bone resorption rates. In the patented disclosures, the effectiveness of any bone resorption modifying agent is determined by measuring the effect on the production of cyclic adenosine-3′5′-monophosphate (c-AMP) using the methods of Rodan et al, J. B. C. Vol 429, page 306, 1974; Rodan et al, Science, Vol. 189, page 467, 1975. In the comparison, the activity shown by the free acid compounds covered by the disclosure of the aforementioned patents ranges from slightly more than half as effective to twice as effective as TCT in stimulating the production of c-AMP.

In contrast to the histologically normal bone resorption resulting from osteoporosis, we also have the more serious osteomalacia or osteitis fibrosa cystica which are illustrative of abnormalities characterized by hypercalcemia.

The most common causes of hypercalcemia are primary hyperparathyroidism and malignant diseases. Total normal plasma calcium concentration ranges from 8.5 to 10.7 mg/dl with about half circulating as free calcium ions. It is the ionized calcium concentration that regulates neuromuscular contractability as well as a variety of other cellular activites. Hypercalcemia occurs when the calcium entry into the blood compartment is greater than the rate of its removal.

In general, patients with mild hypercalcemia (less than 12 mg/dl) do not have symptoms of hypercalcemia and do not experience significant clinical improvement when their calcium level is normalized. Thus, immediate therapeutic intervention is not usually necessary. The decision to treat a patient with moderate hypercalcemia (12 to 14 mg/dl) depends somewhat upon whether the patient is experiencing significant symptoms and also upon the etiology. Usually, however, a series of general measures is instituted at this point (Table I). Most of the therapeutic maneuvers lower serum calcium by increasing urinary calcium excretion.

Hydration is central to the management of hypercalcemia because the pathophysiologic events induced by hypercalcemia (defective renal concentrating mechanism, polyuria, anorexia, nausea, vomiting) invariably cause dehydration and further elevate the serum calcium. A significant decline in the serum calcium level may result simply from restoration of the intravascular volume and glomerular filtration. Rehydration with intravenous saline also has the advantage of improving renal calcium clearance since the degree of calcium excretion is directly linked to the degree of sodium excretion. It is important to use caution in the administration of normal saline, particularly in the elderly or those with cardiovascular or renal disease. The use of a loop diuretic such as furosemide to facilitate sodium and calcium losses may be beneficial in such patients.

TABLE I

| Management of Hypercalcemia | |
|---|---|
| General | Specific |
| Hydration | Mithramycin |
| Saline diuresis | Bisphosphonates |
| Diuresis with loop diuretics | Calcitonin |
| Dialysis | Phosphate |
| Mobilization | WR 2721 (not generally available) |
| | Gallium nitrate |

TABLE I-continued

| Management of Hypercalcemia | |
|---|---|
| General | Specific |
|  | Corticosteroids |
|  | Therapy of underlying etiology |

Another general measure that is usually reserved for the severely hypercalcemic individual is dialysis. Peritoneal or hemodialysis with a low calcium dialysate will lower serum calcium in those patients who are refractory to other measures or who have renal failure.

Patients with severe hypercalcemia (greater than 14 mg/ml) or those who are symptomatic require urgent therapy because they are at significant risk for developing neurologic dysfunction as well as irreversible cardiovascular and renal damage. Excessive calcium mobilization from the skeleton, one of the common pathophysiologic process leading to hypercalcemia, is generally readily controlled by agents that inhibit osteoclast-mediated bone resorption. Mithramycin, a specific inhibitor of osteoclast function, will generally reduce serum calcium regardless of the underlying etiology. A dose of 15–25 ug/kg is administered intravenously over 2 to 4 hours. The infusion is repeated as necessary at 2–4 day intervals. Although side effects of Mithramycin (kidney, liver and bone marrow toxicity) make it of limited usefulness in the setting of chronic hypercalcemia, it is the drug of choice for most life-threatening hypercalcemias.

The bisphosphonates also directly inhibit osteoclast-mediated bone resorption. In the United States, the only available bisphosphonate is ethane hydroxy 1,1-diphosphonic acid (EHDP). EHDP, administered as a daily 2 hour infusion for 3–5 days at a dose of 7.5 mg/kg effectively lowers serum calcium in most settings of increased bone resorption. Other more potent bisphosphonates may be available in the near future.

While calcitonin should theoretically be an ideal agent because it both impairs osteoclast function and increases urinary calcium excretion, it is not as effective as either mithramycin or bisphosphonates. Intravenous phosphate therapy markedly lowers serum calcium, but the associated widespread ectopic soft tissue deposition of calcium-phosphate complexes makes it an unacceptable choice. Oral phosphate therapy may be used to lower serum calcium in patients with low or normal serum phosphorus concentrations but it is not useful in situations of severe hypercalcemia. Doses of less than 3 g per day usually are well tolerated in terms of side effects such as diarrhea.

In patients in whom increased intestinal calcium absorption may constitute a major contributing factor in the pathogenesis of hypercalcemia, glucocorticoids may be effective therapy. Conditions associated with excessive production of vitamin D metabolites (sarcoidosis, vitamin D toxicity, certain lymphomas) fall into this category. Corticosteroids inhibit vitamin D-mediated intestinal calcium transport. In these patients, restriction of both dietary calcium intake and sunlight exposure may also help to control serum calcium.

Specific clinical syndromes characterized by hypercalcemia include "Humoral Hypercalcemia of Malignancy" or "HHM". Many tumors give rise to this syndrome, such as squamous carcinomas (lung, esophagus, cervix, vulva, skin, head and neck), renal bladder and ovarian carcinomas. Breast carcinomas may cause either typical HHM or may lead to hypercalcemia through skeletal metastatic involvement. It has been stated that patients with HHM account for up to 80 percent of patients with malignancy-associated hypercalcemia.

Almost all patients with myeloma have extensive bone destruction. This may occur either as discrete local lesions or diffuse involvement throughout the axial skeleton. This increased bone resorption is responsible for many disabling features including fracture, intractable bone pain and, in some patients hypercalcemia. The bone destruction Which occurs in myeloma is due to an increase in the activity of osteoclasts. It has been found that cytokine lymphotoxin is the major bone resorbing factor produced by cultured human myeloma cells. Clearly there is a great need for safe and effective agents to act in an anti-hypercalcemic capacity.

PRIOR ART

U.S. Pat. Nos. 4,101,668, 4,125,621 and 4,155,108 (Inventors Samour & Vida) which are earlier mentioned disclose, inter alia, compounds which are contemplated herein, but which are employed to ameliorate osteoporis. No hypocalcemic activity is suggested or shown.

In an article appearing in Endrocrinology Vol 117 No. 4 (October 1985) the hypocalcemic effects of thionapthene-2-carboxylic acid is described. One of the coinventors herein is one of the authors of the article.

In a further article appearing in "Calcified Tissue International" Vol 37 PP. 556–559 published 1985 it is stated in the discussion section, "We also found that TNCA could reduce serum calcium concentration in vivo in animals on a low calcium diet or with humoral hypercalcemia of malignancy when this concentration was sustained by increased bone resorption." The authors Raisz et al refer to Raisz et al work with a paper in preparation, that paper is patently the Raisz et al article referred to in "Endocrinology" cited above. The Raisz et al Vol 37 citation is clearly not enabling insofar as teaching the present invention.

DESCRIPTION OF THE PRESENT INVENTION

The present invention relates to a method for treating hypercalcemia in tumor bearing hosts or preventing the onset of hypercalcemia in hosts subsequent tea rapid increase in size of a tumor, and to the compositions useful in such methods.

The compositions useful herein comprise thionapthene-2-carboxylic acid and the pharmaceutically acceptable salts thereof. The cations contemplated include, among others, sodium, potassium, lithium calcium, ammonium and amine. Of particularly outstanding utility are the L-lysine salt, triethanolamine salt, ammonium salt, piperidine and L-arginine salts. The advantages of these amine salts and most especially the lysine and arginine salts are set out in detail in the earlier applications Ser. Nos. 903,385, 086,848 and 739,779 referred to above, and the total disclosures of these applications is hereby incorporated by reference thereto.

The compositions employed in this invention are utilized in dosages effective to prevent the onset of hypercalcemia or to reduce abnormal serum calcium levels to only moderately elevated levels or even to normal levels. The host should be monitored to avoid a hypocalcemic effect.

Generally, it has been found that an oral dose in rats of at least about 0.3 milli (m) mol/kg/day may be effective, although it is preferred to administer at least about 0.6 mmol/kg/day up to about 1.2 to about 1.5 m mol/kg/day. Dosages of 1.2 & 1.5 m mol/kg/day have brought serum calcium levels of from about 13.4 (mg/dl) to about 19.5 have brought such levels to 11.0 or less within 10 hours and these are sustainable through 96 hours. At about 1.8 m mol/kg/day rats become hypocalcemic.

Pharmokinetic studies of thionapthene-2-carboxylic acid (TNCA) in mice, rats, dogs and man and in vitro bone resorption studies in a tissue culture system of fetal rat calvariea, and other in vivo bone resorption inhibition studies in mice and rats suggest that in the present invention dosages of about 60 mg/kg/day or less provide safe and effective therapy in human subjects. Based on these studies, calculations show that dosages in humans would range from about 1 mg to about 60 mg/kg/day. Preferred dosages would vary from about 2 mg/kg/day to about 30 mg/kg/day and more preferred from about 5 mg/kg/day to about 20 mg/kg/day.

The salts of TNCA may be prepared in the manner described in the earlier applications U.S. Ser. No. 903,385 filed Sep. 3, 1986, U.S. Ser. No. 086,848 filed Aug. 17, 1987 and U.S. Ser. No 739,779 filed Jul. 31, 1991. See also European Patent Application 87307807.5 (Publication No. 0259168-published Mar. 9, 1988). As shown in these disclosures, the ammonium and amine salts are simply and efficaciously prepared by adding the TNCA (free acid) to the selected base (e.g., ammonium hydroxide, L-lysine, etc.) in an appropriate solvent e.g., water, methanol. The sodium salt can be prepared by adding the free acid form (TNCA) to sodium ethoxide in methanol. The potassium salt may be formed by adding excess potassium hydroxide and the TNCA to a warm solution of methanol containing a small amount of water.

Convenient liquid oral dosage forms may contain, e.g., from 15 to 200 mg of TNCA (or selected salt). Such preparations may contain the usual adjuvants such as preservatives, humectant, flavor, color and physiologically acceptable salts such as sodium chloride, phosphates and the like.

The liquid preparations may be solutions, suspensions (dispersions) or emulsions. The latter may include pharmaceutically acceptable hydrophobes such as vegetable oils and the like, along with an emulsifying agent such as lecithin, the Pluronics, the Tweens, etc.

Solid dosages forms may be in the form of powders, tablets, capsules, etc. with the active TNCA (or salt) in uncoated or coated (e.g., enteric coating, sustained release-type of coating) form. The usual and conventional binders (e.g., starch, etc.), colorants, flavors, humectants, preservatives, and the like may be included. In addition, other compatible and indicated active ingredients may be formulated with the TNCA (and salts). Examples of these are antibiotics, anti-inflammatories, etc.

The following examples will serve to illustrate the present invention without being deemed limitative thereof. Parts are by weight unless otherwise indicated.

EXAMPLE 1

| Oral Dispersion | |
|---|---|
| TNCA | 15 mg. |
| Sodium chloride | (1) |
| Sodium hydroxide | (2) |
| Phosphate Buffer | (3) |
| Preservative | (4) |
| Humectant | (5) |
| Flavor | (6) |
| Color | (7) |
| Suspending Agent | (8) |
| Distilled deionized water, U.S.P. q.s.a.d. | 1 ml |

(1) Sufficient to maintain constant ionic strength
(2) Sufficient to adjust pH to 7.0 ± 2.
(3) Sufficient to maintain pH to 7.0 ± 2.
(4) e.g., benzyl alcohol, potassium sorbate, methyl and propyl parabens, either alone or in combination; to prevent microbial contamination.
(5) e.g., glycerine, propylene glycol, polyethylene glycol 100 to 10000, either alone or in combination; to prevent evaporation and subsequent crystal growth and/or caplock.
(6) e.g., artificial or natural flavor extracts or solutions, aspartame, saccharine, dextrose, or sucrose; to impart an esthetically acceptable taste.
(7) Water - soluble colorants to impart a desired tint.
(8) See Example 2.

EXAMPLE 2

| Oral Solution | |
|---|---|
| TNCA-L-lysine salt | 50 mg. |
| Sodium chloride | (1) |
| Sodium hydroxide | (2) |
| Phosphate buffer | (3) |
| Preservative | (4) |
| Humectant | (5) |
| Flavor | (6) |
| Color | (7) |
| Distilled deionized water q.s.a.d. to 1 ml | |

(1) Sufficient to maintain constant ionic strength
(2) Sufficient to adjust pH to 7.0 ± 2.
(3) Sufficient to maintain pH to 7.0 ± 2.
(4) e.g., benzyl alcohol, potassium sorbate, methyl and propyl parabens, either alone or in combination; to prevent microbial contamination.
(5) e.g., glycerine, propylene glycol, polyethylene glycol 100 to 1000, either alone or in combination; to prevent evaporation and subsequent crystal growth and/or caplock.
(6) e.g., artificial or natural flavor extracts or solutions, aspartame, saccharine, dextrose, or sucrose; to impart an esthetically acceptable taste.

EXAMPLE 3

| Oral Combination Solution/Dispersion | |
|---|---|
| TNCA-sodium salt | 100 mg. |
| Sodium Chloride | (1) |
| Sodium Hydroxide | (2) |
| Phosphate Buffer | (3) |
| Preservative | (4) |
| Humectant | (5) |
| Flavor | (6) |
| Color | (7) |
| Emulsifying Agent | (8) |
| Distilled Deionized Water q.s.a.d. 1 ml | |

(1) Sufficient to maintain constant ionic strength
(2) Sufficient to adjust pH to 7.0 ± 2.
(3) Sufficient to maintain pH to 7.0 ± 2.
(4) e.g., benzyl alcohol, potassium sorbate, methyl and propyl parabens, either alone or in combination; to prevent microbial contamination.
(5) e.g., glycerine, propylene glycol, polyethylene glycol 100 to 1000 either alone or in combination; to prevent evaporation and subsequent crystal growth and/or caplock.
(6) e.g., artificial or natural flavor extracts or solutions, aspartame, saccharine, dextrose, or sucrose; to impart an esthetically acceptable taste.
(7) Water - soluble colorants to impart a desired tint.
(8) e.g., lecithin, Pluronics, Tweens, Brijs, etc; to produce a stable w/o emulsion of the water solution of TNLY in the external oil phase.

EXAMPLE 4

Example 1 is repeated except that the amount of TNCA is:
(a) 30 mg
(b) 50 mg
(c) 100 mg

EXAMPLE 5

Example 2 is repeated using the following amounts of L-lysine salt
(a) 10 mg
(b) 200 mg
(c) 100 mg
(d) 200 mg

EXAMPLE 6

Example 3 is repeated utilizing the following amounts of the sodium salt of TNCA
(a) 10 mg
(b) 50 mg
(c) 80 mg
(d) 120 mg

EXAMPLE 7

Example 1 and 4 are repeated except that in lieu of the free acid free (TNCA) there are used in separate formulations:
(a) ammonium salt
(b) potassium salt
(c) triethanolamine salt
(d) L-arginine salt
(e) calcium salt
(f) piperidine salt
(g) 1:1 wt. mixture of sodium and potassium salts
(h) 1:1 wt. mixture of potassium and calcium salts
(i) 1:1 wt. mixture of L-lysine and calcium salts As pointed out earlier, severe hypercalcemia requires urgent therapy because of the likelihood of neurologic dysfunction as well as irreversible cardiovascular and renal damage, and while the treatment of the underlying malignancy may have a possible or probable positive prognosis, unless a safe, effective, and lasting antihypercalcemic treatment is available, the patient may succumb to the hypercalcemic effects before the benefits of any treatment of the malignancy can manifest themselves.

The present invention provides a safe and effective treatment utilizing thionapthene-2-carboxylic and the pharmaceutically acceptable salts thereof in formulations as described and exemplified above which can be orally administered to the diseased host.

There is a fairly wide array of compositions for treating hypercalcemia, again as pointed out above, such as mithramycin, bisphosphonates, calcitonin, glucocorticoids, neutral phosphates, among others, but each presents problems. Thus, it has been shown that mithramycin in hypercalcemia patients with lung cancer has a mean duration of effect of five days, must be given intravenously, and there is a risk of serious side effects (marrow suppression, kidney or liver damage). It has been reported that glucocorticoids are effective in fewer than half of the cases and usually a delay of 4 to 5 days before a response is seen; adverse effects are common.

Calcitonin has proved disappointing, the effect is often transient and wears off after 2–3 days.

The diphosphonates, while promising, are not uniformly effective and problems of toxicity have arisen.

The hypocalcemic activity of the compositions useful in this invention is demonstrated in the following examples.

EXAMPLE 8

After an injection of a Walker 256 carcinsarcoma suspension into Fisher 344 rats, the serum calcium concentration remains normal for 7–8 days. Over the following 2–5 days calcium concentration increases above 11 mg/dl coinciding with a rapid increase in tumor size. After obtaining a peak value of 11–18 mg/dl the serum calcium remains stable or decreases until the animal dies. The animals can be expected to survive for 2–3 weeks with persistent hypercalcemia. When TNCA is administered once daily at 0.6 m mol/kg starting on day 9 after inoculation of the tumor cells, serum calcium is 15.2 mg/dl in control rats and 9.4 in the TNCA treated rats on day 12. With calcitonin there is loss of effect after 3–5 days of continuous infusion of the calcitonin.

EXAMPLE 9

In a study similar to that carried out in Example 8 TNCA, given once daily at 0.6 m mol/kg beginning on day 6 after tumor inoculation is found to give a serum calcium of 14.1 mg/dl in the control animals and 8.2 in the treated animals on day 13, 24 hours after the last dose. The mortality is only 4% for rats on the 0.6 m mol/kg regimen whereas it is 28% for the control group during the course of 7 days. Significantly too is the finding that TNCA is effective in animals that have escaped from the hypocalcemic effects of calcitonin.

EXAMPLE 10

Using male Fischer 344 rats implanted with the hypercalcemic Leydig cell tumor, when serum calcium levels are between 11 and 15 mg/dl, the lysine salt of thionaphthene-2-carboxylic is orally administered. The hypocalcemic effects are observable within 10 hours. The following table shows the results at different dosage levels.

The following two examples illustrate tablet dosage forms of TNCA without being deemed limitative thereof.

EXAMPLE 11

| 500 mg Tablets | mg/tablet |
| --- | --- |
| 1. TNCA | 500 |
| 2. Starch 1551 | 125 |
| 3. Lactose, Anhydrous | 157 |
| 4. Explotab | 12 |
| 5. Magnesium Stearate | 9 |
| 6. Water, deionized | q.s. |

EXAMPLE 12

| 50 mg Tablet | mg/tablet |
| --- | --- |
| 1. TNCA | 50.0 |
| 2. Starch 1551 | 12.5 |
| 3. Lactose, Anhydrous | 40.0 |
| 4. Explotab | 4.0 |
| 5. Magnesium Stearate | 1.3 |
| 6. Avicel PH101 | 22.2 |
| 7. Deionized Water | q.s. |

TABLE 2

Effects of TNLY on Serum Calcium Concentration and Survival

| Treatment (mmol/kg/day) | Calcium (mg/dl) at times after initiation of treatment | | | | | Survival (days) |
|---|---|---|---|---|---|---|
| | 0 hr | 10 hr | 24 hr | 48 hr | 96 hr | |
| Control | 13.4 ± 9.8 (11) | 15.9 ± 1.9 (8) | 15.7 ± 1.4 (3) | 18.4 ± 0.7 (5) | 19.5 ± 0.8 (5) | 4.5 ± 0.4 (11) |
| TNLY-0.6 | 13.5 ± 0.7 (14) | 11.6 ± 0.9 (9) | 11.6 ± 1.2 (5) | 13.3 ± 1.5 (4) | 14.8 ± 1.6 (7) | 5.1 ± 0.8 (10) |
| TNLY-0.9 | 13.9 ± 0.8 (15) | 11.5 ± 0.8 (11) | 10.4 ± 1.5 (4) | 11.0 ± 0.6 (5) | — | 5.1 ± 0.6 (13) |
| TNLY-1.2 | 13.8 ± 0.9 (10) | 11.0 ± 0.4 (10) | — | 10.2 ± 0.2 (8) | 9.4 ± 0.2 (2) | 3.5 ± 0.5 (10) |
| TNLY-1.5 | 13.6 ± 1.1 (9) | 10.3 ± 0.7 (9) | — | 9.7 ± 0.3 (5) | 9.0 ± 0.3 (2) | 2.7 ± 0.4 (9) |
| TNLY-1.8 | 13.0 ± 1.6 (4) | 8.9 ± 0.9 (4) | 6.7 ± 1.1 (2) | — | — | 3.0 ± 0.6 (3) |

Values are means ± SEM, with number of animals in parenthesis

The following Table 3 demonstrates the effectiveness of theonapthene-2-L-lysine carboxylate (TNLY) in lowering calcium levels due to bone resorption stimulated by parathyroid hormone (PTH). The unique coaction with calcitonin is also shown. Values reported are means ±SEM for percent of the response to PTH for 2 and 5 day cultures treated with an inhibitor. The lower the values from the control, the more effective the inhibitor.

TABLE 3

'In Vitro" Testing of TNLY in the Presence of Calcitonin

| | 2 days | 5 days |
|---|---|---|
| PTH (Control #1 (25 ng/ml) | 60 ± 7 | 93 ± 6 |
| PTH (Control) #2 (25 ng/ml) | 64 ± 2 | 97 ± 2 |
| Calcitonin 20 mu + PTH (25 ng/ml) | 15 ± 1 | 78 ± 10 |
| Calcitonin 2 mu + PTH (25 ng/ml) | 21 ± 4 | 78 ± 12 |
| Calcitonin 0.2 mu + PTH (25 ng/ml) | 46 ± 5 | 96 ± 1 |
| TNLY $10^{-4}$ mmole + PTH (25 ng/ml) | 36 ± 2 | 79 ± 5 |
| TNLY $10^{-4}$ + Calcitonin 20 mu + PTH (25 ng/ml) | 18 ± 3 | 58 ± 12 |
| TNLY $10^{-4}$ + Calcitonin 2 mu + PTH (25 ng/ml) | 19 ± 3 | 60 ± 10 |
| TNLY $10^{-5}$ + Calcitonin 0.2 mu + PTH (25 ng/ml) | 31 ± 1 | 64 ± 6 |

We claim:

1. A method of preventing or treating hypercalcemia in a tumor-bearing animal which comprises orally administering to the animal a therapeutically effective dose of lysine or arginine salt of thionapthene-2-carboxylic acid.

2. A method as defined in claim 1 wherein the lysine salt of thionaphthene-2-carboxylic acid is administered.

3. A method as defined in claim 1 wherein the animal is a human and the dose ranges from about 1 mg/kg/day to about 60 mg/kg/day.

4. A method as defined in claim 1 which further comprises administering a therapeutically effective amount of calcitonin along with the theionaphthene-2 -carboxylic salt.

5. A method as defined in claim 1 wherein the treatment is begun when the serum calcium level is above normal.

6. A method as defined in claim 4 wherein the animal is a human and the dose of the salt ranges from about 1 mg/kg/day to about 60 mg/kg/day.

7. A method as defined in claim 5 wherein the animal is a human and the dose ranges from about 1 mg/kg/day to about 60 mg/kg/day.

* * * * *